United States Patent [19]

Fan et al.

[11] Patent Number: 5,633,167
[45] Date of Patent: May 27, 1997

[54] REAGENT COMPOSITIONS FOR USE IN SPHERING CELLS

[75] Inventors: Sophie S. Fan, Millwood; Daniel Ben-David, Shrub Oak; Albert Cupo, Scarsdale, all of N.Y.; Gena Fischer, Harrington Park, N.J.; Grace E. Martin, Mount Kisco; Leonard Ornstein, White Plains, both of N.Y.; Gregory M. Colella, Bloomfield, N.J.

[73] Assignees: Bayer Corporation; Mt. Sinai School of Medicine of the City Univ. of New York, both of N.Y.

[21] Appl. No.: 362,744

[22] Filed: Dec. 22, 1994

Related U.S. Application Data

[60] Continuation of Ser. No. 16,323, Feb. 11, 1993, abandoned, which is a division of Ser. No. 802,674, Dec. 5, 1991, Pat. No. 5,284,771.

[51] Int. Cl.$^6$ .................................................. G01N 33/50
[52] U.S. Cl. ........................... 436/17; 436/18; 436/63; 435/1.1
[58] Field of Search ................... 435/1, 4, 5; 436/8, 436/10, 15, 17, 18, 63

[56] References Cited

U.S. PATENT DOCUMENTS

| | | | |
|---|---|---|---|
| 3,684,377 | 8/1972 | Adams et al. | 356/36 |
| 3,883,247 | 5/1975 | Adams | 356/37 |
| 4,325,706 | 4/1982 | Gershman et al. | 436/63 |
| 4,336,029 | 6/1982 | Natale | 436/172 |
| 4,412,004 | 10/1983 | Ornstein et al. | 436/10 |
| 4,490,353 | 12/1984 | Crawford et al. | 424/52 |
| 4,575,490 | 3/1986 | Ornstein et al. | 436/63 |
| 4,652,517 | 3/1987 | Scholl et al. | 435/5 |
| 4,707,451 | 11/1987 | Sage, Jr. | 436/63 |
| 4,735,504 | 4/1988 | Tycko | 356/336 |
| 4,853,338 | 8/1989 | Benezra et al. | 436/15 |
| 4,883,867 | 11/1989 | Lee et al. | 436/63 |
| 4,971,917 | 11/1990 | Kuroda | 436/63 |
| 4,981,803 | 1/1991 | Kuroda | 436/63 |
| 4,985,174 | 1/1991 | Kuroda et al. | 252/408.1 |
| 5,039,613 | 8/1991 | Matsuda et al. | 436/17 |
| 5,075,556 | 12/1991 | Fan et al. | 436/63 |
| 5,242,832 | 9/1993 | Sakata | 436/17 |

FOREIGN PATENT DOCUMENTS

| 2147999 | 5/1985 | United Kingdom. |
|---|---|---|
| PCT/ WO8505640 | 12/1985 | WIPO. |

OTHER PUBLICATIONS

*Cytometry*, vol. 7 (1986) "Flow Cytometry of DNA Content Using Oxazine 750 or Related Laser Dyes with 633 nm Excitation", Shapiro, et al., pp.107–110.

*Analytical Cytology*, 2nd Ed., "The Photometric Chemical Analysis of Cell", in Mellors, R.C., Ed., Pollister A.W. and Ornstein L., McGraw–Hill, New York (1959) pp. 431–518.

*Primary Examiner*—Michael G. Wityshyn
*Assistant Examiner*—Rachel Heather Freed
*Attorney, Agent, or Firm*—Morgan & Finnegan, L.L.P.

[57] ABSTRACT

Methods for blood sample preparation using reagent compositions which include a zwitterionic surfactant for sphering of cells to eliminate orientational noise. When the reagent composition including a dye for staining a subset of cells is reacted with a blood sample, and the reaction mixture is passed through the sensing region of a flow cytometer, the light scattered and absorbed by each cell is measured, the stained cells can be distinguished from the unstained cells, and when the cells are reticulocytes and mature erythrocytes, respectively, the volume and hemoglobin concentration of each reticulocyte or erythrocyte, and the hemoglobin content, mean cell volume, mean corpuscular hemoglobin concentration, and mean cell hemoglobin of the reticulocytes or erythrocytes are calculated from the measured cell-by-cell volume and hemoglobin concentration.

10 Claims, 13 Drawing Sheets

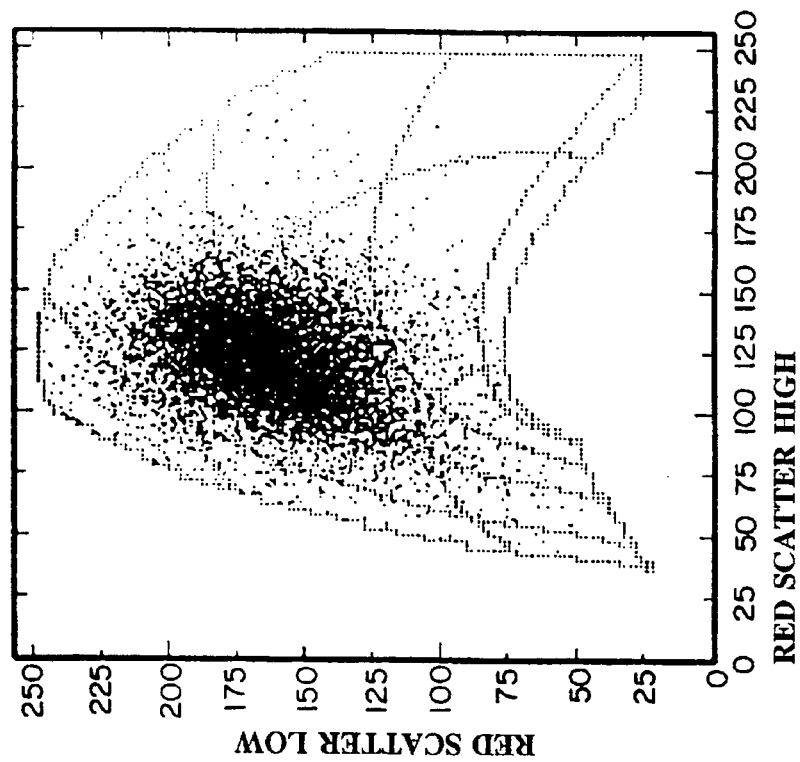
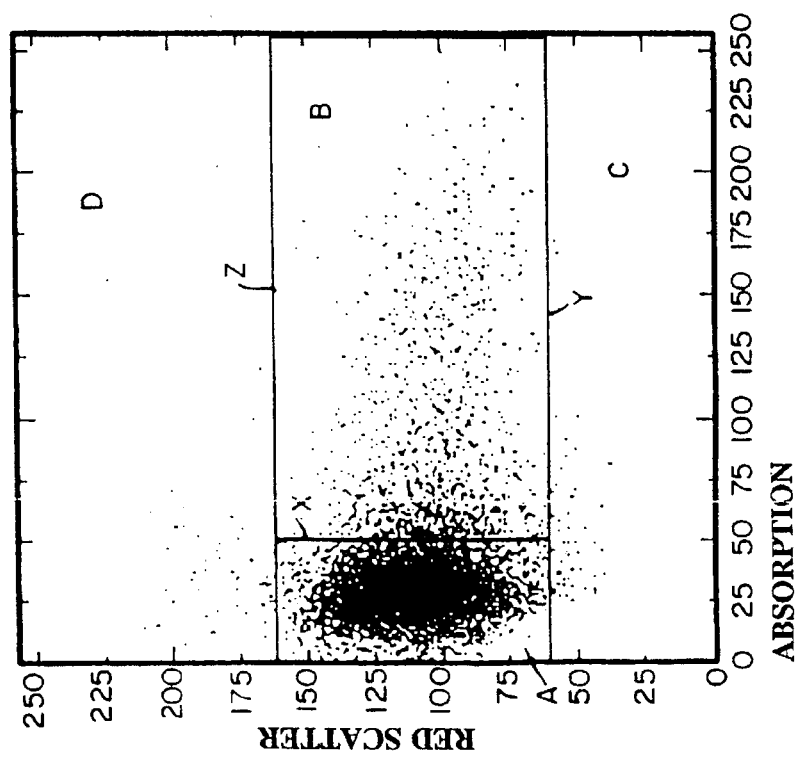
FIG. 5B
FIG. 5A

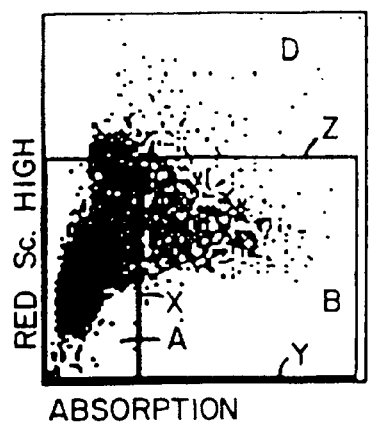
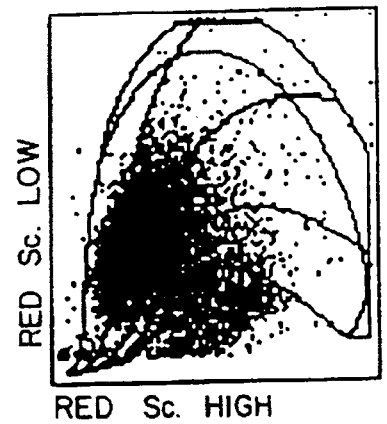
FIG. 8A  FIG. 8B
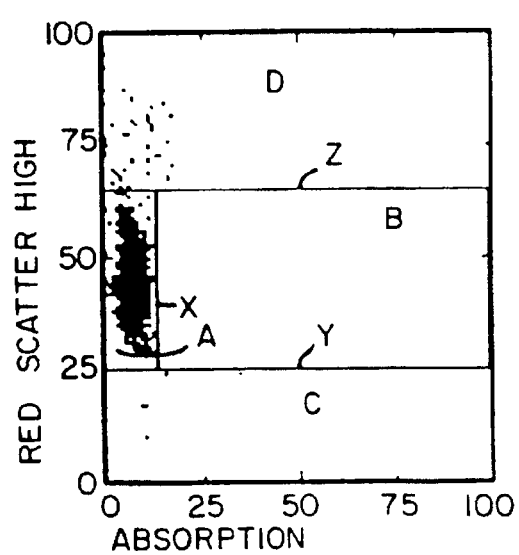
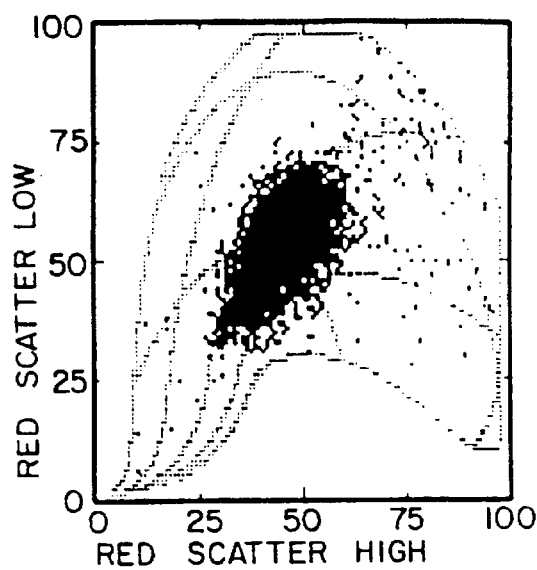
FIG. 8C  FIG. 8D

REAGENT COMPOSITIONS FOR USE IN SPHERING CELLS

This is a continuation of application Ser. No. 08/016,323, filed on Feb. 11, 1993, now abandoned, which is a divisional of application U.S. Ser. No. 07/802,674, filed Dec. 5, 1991, now U.S. Pat. No. 5,284,771.

BACKGROUND OF THE INVENTION

1. Field of the Invention

The present invention relates to reagent compositions and their use in cell analysis, and, more particularly, to reagent compositions and their use in preparing whole blood samples for improved electrooptical determination of the volume and/or protein concentration, protein content and/or nucleic acid content of large numbers of cells by light scatter and absorption and/or fluorescence flow cytometry techniques.

2. Description of the Prior Art

At the birth of the field of cytophotometry, the science of the quantitative determination of the properties of individual cells by measuring their interactions with beams of light (usually through various kinds of microscopes), Caspersson (Caspersson T., *Skand, Arch, Physiol,*, 1936, 73 Suppl. 8, 1–151) pointed out that by focusing a point source of light at the center of a spherical cell, one was assured that all optical paths through the cell would be precisely the same and equal to the cell diameter. In principle, this would permit accurate measurement of the concentration of a light-absorbing species of molecules from the measured optical density of the cell (Pollister, A. W. and Ornstein, L., "The Photometric Chemical Analysis of Cell", in Mellors, R. C., Ed., *Analytical Cytology*, 2nd Ed., McCraw-Hill, New York, 1959, 431–513). Yet about 50 years passed before it was demonstrated that, by controlled conversion of non-spherical cells into perfect spheres, the analysis of flow cytometric data of light scattered by cells could be vastly improved (see Kim and Ornstein, and Tycko discussed below). The further improvement in such controlled sphering of this invention now substantially extends the utility of controlled sphering of cells to its use for the sensitive measurement of minute quantities of absorbing molecules in cells by absorption/scatter flow cytometry as well as for the accurate simultaneous measurement of cell volume and cell total protein concentration (or equivalently, refractive index, density or total cell solids) by the Tycko method.

In all the higher animals, blood consists of an aqueous fluid part (the plasma) in which are suspended corpuscles of various kinds: the red blood cells (erythrocytes), the white blood cells (leukocytes) and the blood platelets. Plasma has a composition comprising roughly 90% water, 9% protein, 0.9% salts and traces of other materials such as sugar, urea, uric acid and the like.

The cells or corpuscles of the peripheral blood (i.e., the blood outside the bone marrow) are divided into two main groups: erythrocytes, whose primary object is to transport oxygen and leukocytes, whose primary functions relate to the immune system and the destruction of materials foreign to the body. In addition to these two main groups, the blood also contains the so-called blood platelets which are important in hemostasis.

The final stages of erythrocyte maturation occur after their release from the bone marrow while these cells are circulating in the peripheral blood. These young red cells, or "reticulocytes", have lost their nucleus, and thus, their ability to divide or to synthesize ribonucleic acid (RNA). Although these functions have ceased, reticulocytes are still metabolically active and for a while are capable of synthesizing protein, taking up iron for the synthesis of heme, and carrying out the necessary metabolic reactions required to maintain an energy-rich state. These cells are usually most easily distinguished from mature erythrocytes by exposing them to solutions of cationic dyes which react with the anionic RNA in the reticulocytes and precipitate into a fine or coarse stained "reticulum" within the reticulocytes, which gives the reticulocytes their name.

Although reticulocytes normally comprise about 0.5 to 2 percent of the total red blood cell population, this percentage can change dramatically under abnormal conditions. For example, reticulocyte counts have been used for many years as a diagnostic aid in studying blood dyscrasias and as an index of red blood cell regeneration following hemorrhage, as well as for monitoring early toxicity in chemotherapy of certain malignant diseases.

Nucleic acids (RNA and DNA) are polyanions which can be stained with practically any cationic dye. The RNA in reticulocytes can be stained with only a few cationic dyes [including Brilliant Cresyl Blue (BCG), New Methylene Blue (NMB), Auramine O (AuO), Acridine Orange (AO), Thiazole Orange (TO) and Pyronine Y (PY)]. Among these dyes, only a sub-set can be made to penetrate the cells (and therefore stain) rapidly. The sub-set includes NMB and AO. The rate of, and degree of staining of reticulocytes depends upon the extracellular concentration of the dye, the rate of penetration of the dye through the reticulocyte membrane, and the strength of the specific binding constant between the cationic dye and the reticulocyte RNA. The latter two properties are different, and not easily predictable, for each dye, so that trial and error are necessary to discover useful reticulocyte stains. Not all cationic substances are capable of penetrating intact red cell (and reticulocyte) membranes, and the nature of the anions which necessarily accompany the cations, can effect whether or not the cationic substance penetrates rapidly, slowly or not at all. Hydrophobic molecules generally penetrate red cell membranes faster than hydrophilic molecules, and small molecules generally penetrate membranes faster than large molecules. Only a sub-set of salts or buffers mixed with those cationic dyes which can stain reticulocytes permit rapid staining; that is the "right" dye with the "wrong" buffer can take "forever" to stain reticulocytes. Again, trial and error are necessary to discover useful formulations of reticulocyte staining mixtures. Thus, despite various "rules" which can be used as guides, it is not yet possible to predict, a priori, whether, and under which conditions any particular cationic dye may rapidly penetrate and stain reticulocytes.

The fundamental concept of flow cytometry is essentially the passing of cells, one at a time, through a specific sensing region. Typically, by means of hydrodynamic focusing, single cells are passed through the sensing zone, which consists of a focused light source and a detection system for the measurement of scattered, absorbed or fluorescent light.

The effect a particle has on the light it intercepts can be detected in a number of ways. In general, the particle has a refractive index which is different than that of the medium in which it is suspended. It will therefore scatter light with which it is illuminated through a range of angles, and with varying intensities, that depend upon that refractive index difference, the particle's size, its shape and any internal variations in refractive index and structure as well as upon the wavelength of the illuminating light. (For homogeneous spheres, Mie Scattering Theory provides a complete description of the distribution and intensities of scattered light.) A particle may also absorb some of the incident light. In the latter case, a portion of the absorbed light may be reemitted as fluorescence, typically at a longer wavelength than the wavelength of the absorbed light.

These and other effects can be measured with light detectors arranged to measure different angular intervals of scattered light, of unscattered light and of fluorescent light.

When particles are as small as cells, typically less than 15 micrometers in diameter, the numbers of photons in the illuminating beam affected by their passage at high speed (typically hundreds to thousands of widely-spaced cells per second), and especially compared to the number of photons per second falling on the illuminated part of the suspension stream, [and compared to the background illumination of an absorption detector (and even a fluorescence detector)] can be very small. Therefore, the limits of sensitivity of detection of small particular differences between particles depends critically on the photon flux (which depends at least on the intrinsic "brightness" of the light source) and how large the perturbations of the photon flux are that are produced by other small and large differences between particles.

The main sources of interfering noise in absorption, scatter and fluorescence flow cytometry signals can be quite different for each kind of signal. To a first order approximation, the magnitudes of fluorescence signals from stained or unstained cells are almost uninfluenced by shape or orientation of the cells from which the signals arise, whereas scatter and absorption signals are very strongly influenced by shape and orientation. As an extreme example, the native biconcave shape of human erythrocytes has a profound effect on the absorption and scatter signals they generate; effects larger than the small absorption signals of typical classically stained reticulocytes (see FIGS. 8A–8D). This is the main reason why, prior to the present invention, absorption flow cytometry methods have not been useful for reticulocyte counting or generally for the measurement of low concentrations of absorbing molecules in cells. On the other hand, weakly fluorescence materials in cells or (for example, unbound fluorescent dyes) in their surrounding medium has virtually no effect on absorption or scatter signals.

Several semi-automated methods are available which can be used for counting the percentage of reticulocytes in an anti-coagulated sample of whole blood. In each of the existing methods, a diluent containing an organic cationic dye, such as AO, AuO or TO, is used to stain the RNA within the reticulocytes. The dye penetrates the cell membrane, binds to the RNA and usually precipitates a "reticulum" within each reticulocyte. The amount of signal from stained RNA is roughly proportional to the RNA content. After proper staining, a fluorescence flow cytometer, equipped with the proper excitation light source (typically an argon ion laser emitting at 488 nm), and emission detection system, can be used to determine the percentage of reticulocytes in the effluent.

Illustrative methods for differentiating reticulocytes in whole blood samples using fluorescent dyes and flow cytometric methods are disclosed in the patent literature.

For example, U.S. Pat. No. 3,684,377 to Adams and Kamentsky discloses a dye composition for differential blood analysis including an aqueous solution of acridine orange having a pH factor and osmolality within normal physiological ranges for human blood. The dye composition can be used for counting reticulocytes by measuring the presence or absence of a fluorescence signal with an erythrocyte scatter signal.

U.S. Pat. No. 3,883,247 to Adams discloses a similar method to that of Adams and Kamentsky using a dye composition including acridine orange having a concentration of between $10^{-6}$ and $10^{-5}$ grams per ml.

U.S. Pat. No. 4,336,029 to Natale discloses a reagent composition comprising an aqueous solution of the dye AO, citrate ion and paraformaldehyde at a pH of about 7.4 and an isotonic osmolality. The concentrations of the various ingredients were selected to maximize dye uptake of the reticulocytes and platelets, and provided for dye uptake to be achieved within 2–5 minutes of mixing the blood sample and reagent composition. An automated method for detection of platelets and reticulocytes utilizing the Natale reagent is disclosed in U.S. Pat. No. 4,325,706 to Gershman, et al.

In the reagent disclosed in U.S. Pat. No. 4,707,451 to Sage, Jr., reticulocytes are stained with thioflavin T or chrysaniline. A whole blood sample was found to be effectively stained by mixing a 25 µl aliquot of the dye in an isotonic saline solution (0.2 mg/ml) with 10 µl of anticoagulated whole blood with the mixture incubated for about 7 minutes.

U.S. Pat. No. 4,883,867 to Lee, et al. discloses a dye composition for staining RNA or DNA. The staining composition includes TO as the preferred dye compound. The reticulocytes are stained in a minimum time of 30 minutes.

A reagent for reticulocyte counting with flow cytometric techniques is described in U.S. Pat. No. 4,971,917 to Kuroda which contains a carbonate salt to reduce the non-specific staining of the mature erythrocytes by the dye, e.g. AuO, to prevent the mature erythrocytes from being erroneously counted as reticulocytes when analyzed by fluorescence flow cytometry.

U.S. Pat. No. 4,981,803 describes a reagent for reticulocyte counting which comprises two solutions, namely a stock solution for staining in which a dye AuO is dissolved in a non-aqueous solvent and a buffer solution which satisfies the optimum staining conditions.

Another reticulocyte staining reagent for fluorescence flow cytometric techniques including AuO is disclosed in U.S. Pat. No. 4,985,174 to Kuroda, et al. This reference teaches an incubation time of the reagent and sample of anywhere between 30 seconds and 20 minutes.

As noted above, only a small sub-set of cationic dyes selectively stain reticulocytes, and only a smaller sub-set of these penetrate reticulocytes rapidly. The cationic dye compounds of the present invention stain the reticulocytes in less than 5 minutes so that reticulocyte analysis by flow cytometry can be performed shortly after the blood sample and the reagent composition are mixed together, thus making the present invention readily adaptable for automated procedures.

Quaternized AO derivatives for quantitating reticulocytes are described in U.S. patent application Ser. No. 07/444,255 filed Dec. 1, 1989 by Fan and Fischer entitled "Compounds and Reagent Compositions and Their Use in the Quantitative Determination of Reticulocytes in Whole Blood", now U.S. Pat. No. 5,075,556 which is incorporated herein by reference. The Fan, et al. reagent contains $10^{-6}$ gram per ml of an AO derivative in a buffer solution including paraformaldehyde and potassium oxalate. This reagent composition stains reticulocytes to enable the quantitative fluorescence flow cytometric analysis of reticulocytes in a blood sample. Neither this reagent nor any of the above-mentioned reagents contain a sphering agent to prevent orientational noise problems as discussed below, and none permit simultaneous determination of other diagnostically significant parameters such as volume and hemoglobin concentration of the reticulocytes and erythrocytes on a cell-by-cell basis.

Shapiro and Stephens disclose the use of Oxazine 750 for the determination of DNA content by flow cytometry in *Flow Cytometry of DNA Content Using Oxazine 750 or Related Laser Dyes With 633 nm Excitation*, Cytometry, Vol. 7, pp. 107–110 (1986). The cells are stained by 10 µM to 30 µM of Oxazine 750, and are fixed by the addition of ethanol for the DNA determination. Shapiro and Stevens claim that Oxazine 750 does not appear to stain RNA. Moreover, such protocols with Oxazine 750 do not permit reticulocyte counting or simultaneous determination of other diagnostically significant red blood cell parameters such as volume and hemoglobin concentration on a cell-by-cell basis.

As mentioned above, a disadvantage of reticulocyte quantitation through the use of an absorption or scattered light flow cytometer is the inability to differentiate between orientational noise and reticulocyte signals. Human and many other mammalian red blood cells have the shape of biconcave disks. The amount of light scattered by such asymmetric red blood cells varies with the orientation of the cell. Accordingly, two identical red blood cells will generate very different scattered light and absorption signals as they pass through the sensing zone unless their orientations in the zone are identical. The result is that the distribution of magnitudes of scatter and absorption signals for normal red cells is very broad and bimodal (see FIGS. 8A and 8B). Two red blood cells which are identical, except for the presence in one of a small amount of stained reticulum, generally produce large signal differences on scattered light and absorption detectors because of their different orientations. When this occurs, the very small difference the stained reticulum might generate is buried in the orientational noise.

U.S. Pat. Nos. 4,575,490 and 4,412,004 to Kim and Ornstein teach a method for the elimination of orientational noise in the measurement of the volume of red blood cells in a flow cytometer. Their method involves isovolumetric sphering of unstained red blood cells to eliminate any orientational differences between the cells to permit more precise and accurate measurement of cell volume. Each red blood cell is converted from a biconcave shape to a perfect sphere by a surfactant sphering agent. A "buffering" protein and/or an aldehyde fixing agent are used with the sphering agent to prevent lysis of the erythrocytes. The anionic surfactants described by Kim and Ornstein cannot be used with reticulocyte stains because they have been found to react rapidly with and precipitate the cationic dyes used to stain and precipitate the reticulum.

U.S. Pat. No. 4,735,504 to Tycko discloses the red blood cell channel of the TECHNICON H·1 system, a flow cytometer which provides a fully automated method and means for determining the individual and mean erythrocyte volumes (MCV), and individual and mean corpuscular hemoglobin concentrations (MCHC) of the erythrocytes in an anticoagulated whole blood sample. In this method, the red blood cells in a two microliter aliquot of a whole blood sample are first diluted, and then isovolumetrically sphered using the Kim and Ornstein method just described. After a twenty second incubation period, these cells are passed, essentially one at a time, through the illuminated measurement zone within the red cell channel of the analyzer. The magnitude of the light scattered by these cells into two separate angular intervals is measured. The choice of light source and detection angles are critical in this application. When the light source is a helium neon laser, which emits light at 633 nm, the two scattered light collection angle intervals are two to three degrees (2°–3°) and five to fifteen (5°–15°) degrees. Once the level of the scattered light in each interval is known for a cell, the volume and hemoglobin concentration for that cell are determined by comparison with values predicted by Mie scattering theory. The volume (V) and hemoglobin concentration (HC) for each cell are stored in memory, and the MCV and MCHC are calculated at the completion of the sample measurement cycle by techniques known in the art as discussed in Tycko. The V and HC distribution cytogram and the V and HC histograms are produced using these calculations.

Neither of the above methods distinguishes between reticulocytes and non-reticulocytes, and the methods as previously described and practiced cannot be used to determine separately, the diagnostically significant parameters of the reticulocytes and erythrocytes such as volume and hemoglobin concentration on a cell-by-cell basis.

Another difficulty in monitoring reticulocyte counts with a flow cytometer is difficulty in differentiating between reticulocyte detection signals, mature red blood cell signals, and system noise. The stained strands of RNA are numerous in young reticulocytes, and generate signals of relative large magnitude when detected by a flow cytometer. However, more mature cells contain less stained RNA, and generate smaller signals which may be masked by the noise of the flow cytometer measuring system.

There exists a need for methods and reagents useful for identifying reticulocytes and simultaneously measuring separately the volume, hemoglobin concentration and hemoglobin content of reticulocytes and erythrocytes in a whole blood sample by light scatter and absorption or fluorescence flow cytometry techniques.

We started with the premise that we wanted to use a cationic dye in a variant of well-known art to stain the reticulum. We were also interested in developing flow cytometric methods which could utilize fluorescence and/or absorption to detect reticulocytes. In addition, in the case of absorption, we wanted to use the sphering of red cells to eliminate orientational noise (see FIGS. 8C and 8D). (Note, that if one is not concerned about also simultaneously recovering and measuring precisely the original cell volume, it is not necessary for the sphering to be isovolumetric or complete to eliminate most orientational noise.) We also hoped, by using isovolumetric sphering and the aforenoted methods of Tycko, that for fluorescence and absorption methods, we would be able to simultaneously measure reticulocyte and mature red cell volume and hemoglobin on a cell-by-cell basis using a reagent which also selectively stained reticulocytes. (Note, if the sphering is complete, not isovolumetric, but some known factor X of isotonicity where X varies from about 0.5 to 2 [from 0.15 to 0.60 Osm] using Tycko's method with a correction by 1/X for volume and a correction by X for protein [e.g. hemoglobin] concentration, original values can be calculated.)

These inventions are the subject of co-pending U.S. application Ser. Nos. 07/802,585 and 07/802,593, both filed Dec. 5, 1991, both entitled "Reagent Compositions and Their Use in the Identification and Characterization of Reticulocytes in Whole Blood", filed concurrently herewith and assigned to the assignees of the present invention, the disclosures of which are incorporated herein by reference.

To utilize Tycko's method, a light source which emits monochromatic light in a region where hemoglobin is very transparent is required; typically a light source like a red helium neon (HeNe) laser, or a laser with even longer wavelength. This means that if that wavelength is also to be used for the absorption measurement, the dye must be a blue dye with a strong absorption of red light.

We explored non-ionic, cationic and zwitterionic surfactants for compability with cationic dyes, and as red cell sphering agents as would be suggested by the teaching of Kim and Ornstein. As in the Kim and Ornstein method, we used a protein (typically bovine serum albumin) to "buffer" the concentration of the surfactants to slow down red cell lysis. A number of such surfactants (e.g., Triton X100 and Laurylpropylamidobetaine) worked satisfactorily. We then inadvertently discovered that Laurylpropylamidobetaine and some other zwitterionic surfactants (e.g. DDAPS and TDAPS) did not require protein buffering to delay red cell lysis, and are ideal alternate sphering agents for all kinds of blood cells for the methods of Kim and Ornstein. Because they do not require protein buffering, they permit a stable and simpler reagent to be manufactured. (The fixing steps of Kim and Ornstein are no longer obligatory; alternately, the problems of bacterial growth in protein-containing reagents is also avoided.)

SUMMARY OF THE INVENTION

Accordingly, it is a principal object of the present invention to provide an improved reagent composition and method for sphering cells in a blood sample to reduce or eliminate orientational noise.

Another object of the present invention is to provide a reagent composition and method as above for the sphering of red blood cells.

Still another object of the present invention is to provide a reagent composition and method as above for the simultaneous sphering of red blood cells and reticulocytes and staining of reticulocytes.

A further object of the present invention is to provide a reagent composition and method as above for simultaneously determining the volume, hemoglobin concentration and hemoglobin content of reticulocytes and erythrocytes in a whole blood sample by absorption and scattered light flow cytometry.

Still yet another object of the present invention is to provide a reagent composition and method as above for simultaneously discriminating between and counting each of the red blood cells and the reticulocytes within a blood sample, and determining the volume, hemoglobin content, hemoglobin concentration, mean erythrocyte volume, and mean corpuscular hemoglobin concentration of each cell type determined from measurements on a cell-by-cell basis.

In accordance with one embodiment of the present invention, a reagent composition includes an organic cationic dye for staining the reticulocytes and a buffer solution for maintaining pH of about 6 to about 9. The dye may be the blue absorption dye Oxazine 750 (available from Exciton, Inc. of Dayton, Ohio) having the structure:

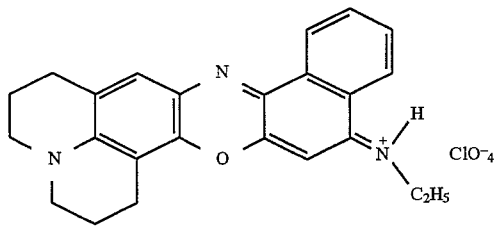

or the blue absorption dye New Methylene Blue having the structure:

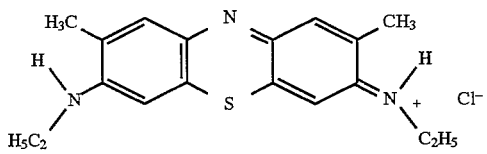

The buffer system of the reagent composition includes suitable buffers to maintain the pH of the reagent composition between about 6 and about 9. The solution may include one or more of the following constituents at the concentration noted, with the final osmolality adjusted with KCl or NaCl to from about 250 m Osm to about 330 m Osm:

| Constituent | Concentration (mM) |
| --- | --- |
| K/Na HCO$_3$ | 5–50 |
| Mg Cl$_2$ | 0–88 |
| KCl | 4–104 |
| Na$_3$PO$_4$ | 0–1.5 |
| CaCl$_2$ | 0–0.6 |

Preferably, the solution is formulated to maintain the pH of the reagent composition at between about 7 to about 8, and may include one or more of the following constituents in the concentration ranges given, and maintains an osmolality of from about 280 m Osm to about 300 m Osm:

| Constituent | Concentration (mM) |
| --- | --- |
| Tris/TEA | 0–150 |
| K$_2$Ox/EDTA | 0–121 |
| KCl/NaCl | 0–155 |

It has been found that the reagent composition should contain certain anions and cations to facilitate the dye penetration through the red cell membrane. Such anions may include bicarbonate, chloride, borate, barbital, oxalate (Ox) or ethylenediaminetetraacetic acid (EDTA). But not all anions have been found effective in promoting dye penetration across the cell membranes. For example, when one or more of the following anions: malate, tartarate, phosphate, were included in the reagent compositions as the only major anions, little, if any, distinction could be made between reticulocytes and erythrocytes. Possible cations include potassium, sodium, trishydroxymethylamino (Tris), or triethanolamine (TEA).

The reagent composition may be used to identify reticulocytes in a whole blood sample using the technique of scatter/absorption flow cytometry. The method in its broadest application includes mixing an aliquot of whole blood with one of the above reagent compositions. After a suitable incubation period, the sample/reagent mixture is then passed, one cell at a time, through a specific sensing region of the flow cytometer. By means of hydrodynamic focusing, single cells are passed through the sensing zone, where they are illuminated by a focused light source having a suitable illumination wavelength. At least one scattered light signal and at least one absorption signal are measured for the cells on a cell-by-cell basis. From these measurements, the reticulocytes can be distinguished from the erythrocytes.

In accordance with the preferred embodiment of the present invention, the above reagent composition further includes a zwitterionic surfactant to isovolumetrically sphere the red blood cells and reticulocytes. The zwitterionic sphering agent is preferably an alkyl amido betaine or an alkyl betaine such as lauramidopropylbetaine (LAB), cocoamidopropylbetaine (CAPB) and cocoamidosulfobetaine (CASB). Other preferred sphering agents are N-tetradecyl-N, N-dimethyl-3-ammonio-1-propanesulfonate (TDAPS) and N-dodecyl-N, N-dimethyl-3-ammonio-1-propanesulfonate (DDAPS). TDAPS and DDAPS are most preferred sphering agents because they give the most stable sample preparation.

To effectively isovolumetrically sphere the reticulocytes and red blood cells within a blood sample, the concentration of the sphering agent in the reagent composition is from about 3.9 µg/ml to about 148 µg/ml. The sphering agent is preferably present in an amount of from about 12 µg/ml to about 87.5 µg/ml of LAB; from about 3.9 µg/ml to about 11.8 µg/ml of TDAPS; from about 49.3 µg/ml to about 148 µg/ml of DDAPS; from about 8.8 µg/ml to about 17.5 µg/ml of CAPB; or from about 12.5 µg/ml to about 15 µg/ml of CASB.

We have found that, in the presence of the buffer systems described above, the concentration of New Methylene Blue in the reagent composition required for staining RNA is in the range of from about 10 to 100 µg/ml.

We have found, for example, that in the presence of the buffer systems described above, the concentration of Oxazine 750 in the reagent composition required for RNA staining is low, i.e., in the range of from about 2 µg/ml to about 15 µg/ml, and the buffer enhanced penetration results in the dye staining RNA in the reticulocytes in less than 5 minutes. Such a low concentration of dye minimizes non-reticulocyte staining of mature erythrocytes which leads to a good signal separation from the noise background. Such rapid staining makes the reagent composition highly compatible with automated methods.

When this whole blood/reagent composition mixture is passed through the sensing region of a flow cytometer, the light scattered and absorbed by each cell is measured, the erythrocytes can be distinguished from reticulocytes and the volume and hemoglobin concentration of each reticulocyte or erythrocyte can be determined. The number of reticulocytes and erythrocytes, and the hemoglobin content, mean cell volume, mean corpuscular hemoglobin concentration, and mean cell hemoglobin of the reticulocytes or erythrocytes are calculated from the measured cell-by-cell volume and hemoglobin concentration.

The invention accordingly comprises the compositions and methods hereinafter described, the scope of the invention being indicated in the claims.

BRIEF DESCRIPTION OF THE DRAWINGS

The above and other objects and significant advantages of the present invention are believed made clear by the following detailed description thereof taken in conjunction with the accompanying drawings wherein:

FIGS. 5A and 5C are cytograms of red light scatter vs. red absorption, and FIGS. 5B and 5D are cytograms of red light low angle scatter vs. red light high angle scatter for a whole blood sample containing completely sphered red cells and reticulocytes stained with Oxazine 750 and New Methylene Blue, respectively, with pseudo-absorption correction in accordance with Example 3;

FIGS. 8A and 8B are cytograms of red light scatter vs. red absorption, and red light high angle scatter vs. red light low angle scatter, respectively, for unstained, unsphered red blood cells; 8C and 8D are similar cytograms for unstained, sphered red blood cells; FIG. 8C has been corrected for pseudo-absorption.

DESCRIPTION OF THE PREFERRED EMBODIMENTS

Figure 1A:
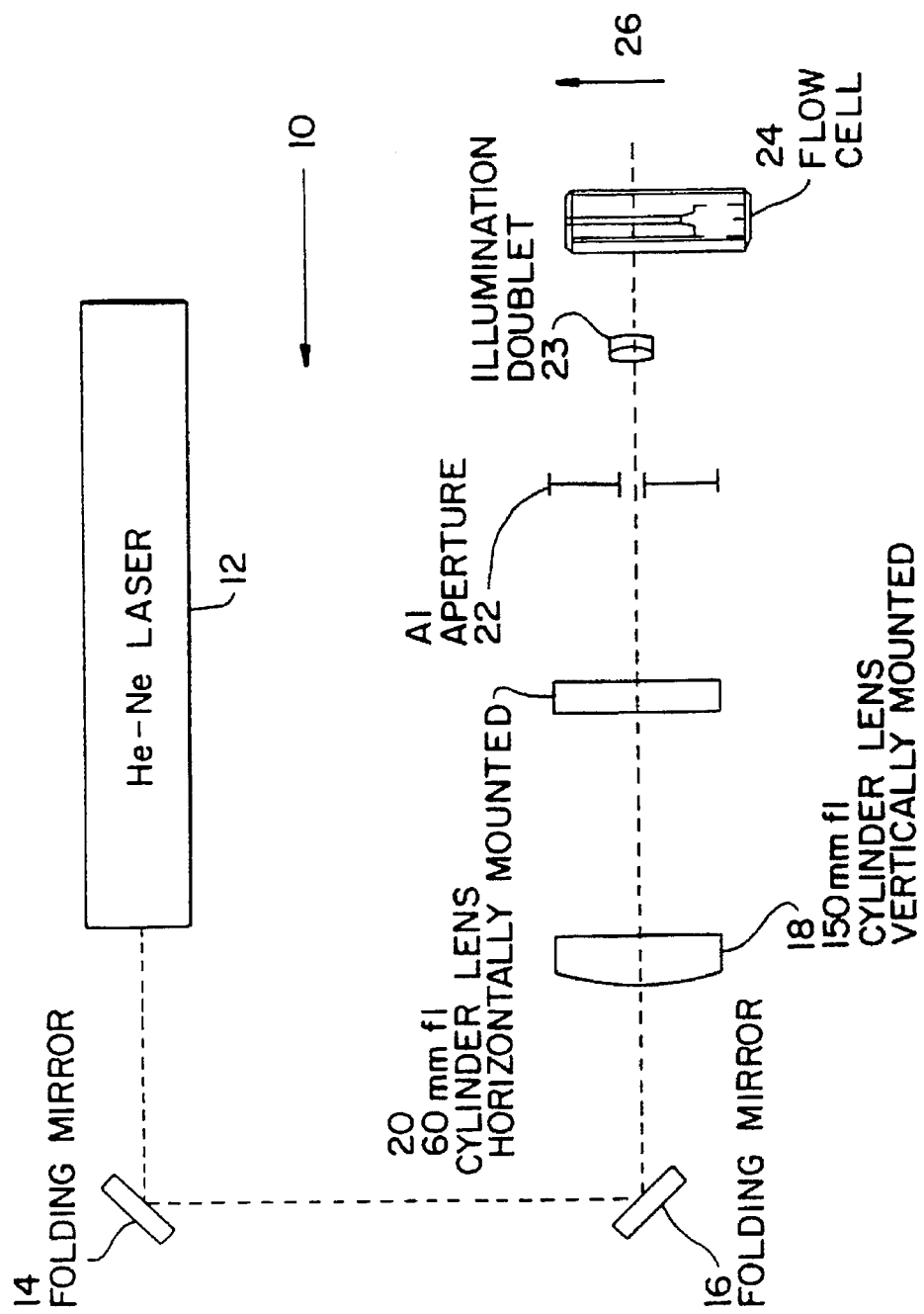
FIGS. 1A, 1B and 1C are schematic representations of the illumination optics, detection optics and detection signal processing system, respectively, of a scatter/absorption flow cytometer for practicing the principles of the present invention.
Figure 1B:
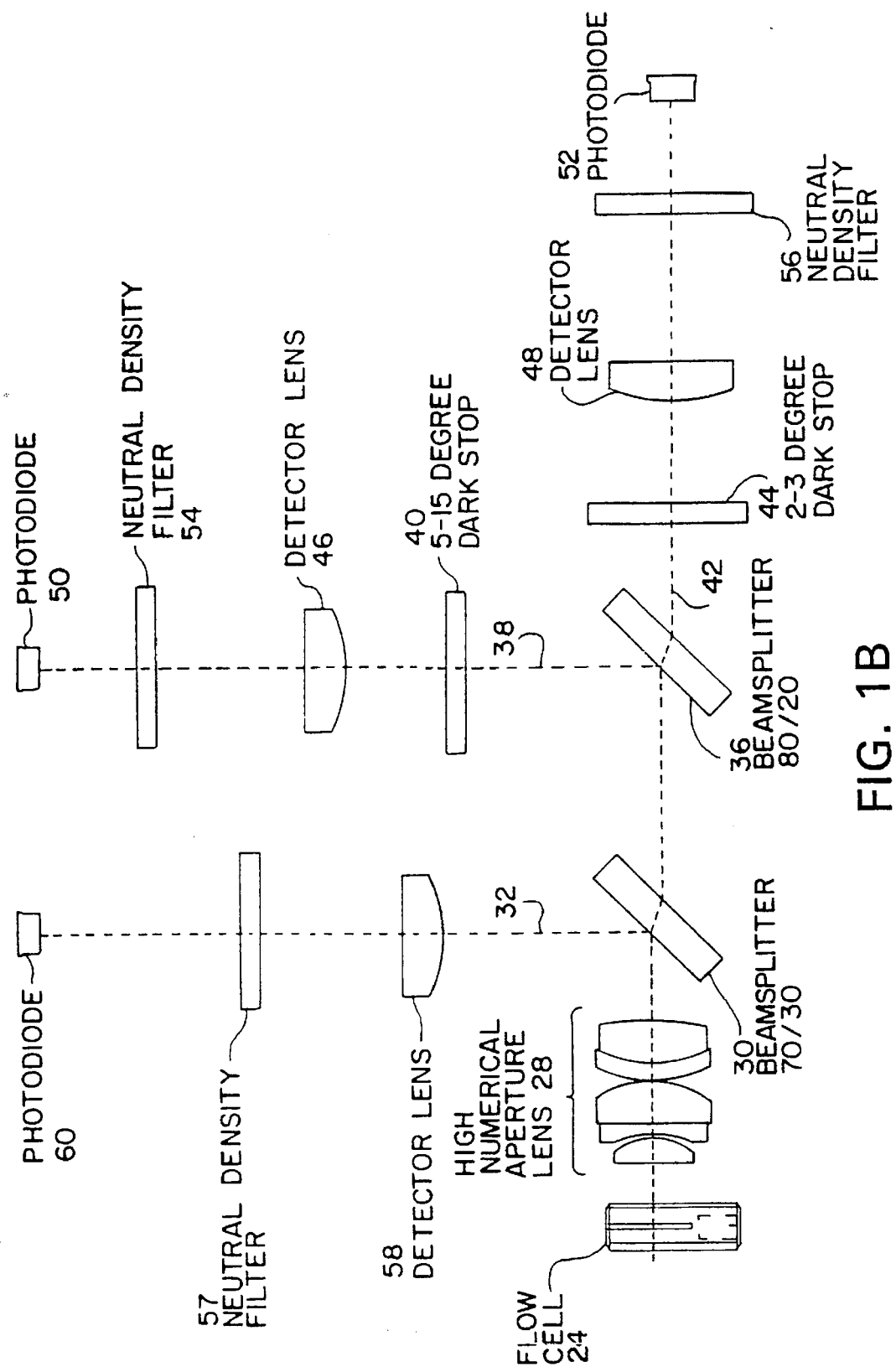

Referring to FIGS. 1A and 1B, there are shown stylized, functional and structural representations of portions of a flow cytometric apparatus which may be utilized in practicing the principles of the present invention. In fact, the apparatus depicts a particular system which is a modification of a system commercially available under the trade designation TECHNICON H·1, sold by the assignee hereof.

The apparatus incorporates the principles of flow cytometry for cell analysis, and includes the capacity for sensing the light scattering and light absorption responses of cells to specific types of illumination. Only those components of primary interest with respect to the invention are shown. Thus, the drawings do not illustrate all of the mechanical and electrical elements, i.e. motors, solenoids, pumps, valves, sensors, required for driving and controlling the various components of the apparatus. All of these elements may have any known, conventional form, which can readily be realized by one of normal skill in the art having knowledge of the information hereinafter given with regard to the desired mode of operation of the various components in a flow cytometric apparatus according to the invention for treating the samples in the manner intended.

Described in its most general terms, a sheath-stream flow-cell and supporting hydraulics deliver prepared cells to the point of measurement. The cells are confined to a cylindrical volume which is central to the square-cross-section flow channel of the flowcell. The flowcell construction is identical to that used in the TECHNICON H·1 system. The hydraulic system is quite simple, consisting of only two peristaltic pumps and their associated tubing. The sheath pump and tube deliver the sheath at a rate of $1.6 \times 10^{-7}$ m$^3$/sec; the sample is delivered at a rate of $3.5 \times 10^{-10}$ m$^3$/sec; the flow channel within the flowcell is 250 µm by 250 µm. The resulting cylindrical sample stream flowing axially within the sheath stream has a diameter of 7 µm and a velocity of 2.5 m/s.

The primary objective is to provide an optical system which will support an absorption measurement, in addition to the two red cell scatter channels provided by the TECHNICON H·1 system. The optical system of the scatter/absorption flow cytometer can be divided generally into two subsystems: a) the illumination optics (FIG. 1A); and b) the detection optics (FIG. 1B).

Referring first to FIG. 1A, the illumination optical system is generally identified by the reference numeral 10, and incorporates a helium-neon laser 12 that emits a 2 mW beam of light at 633 nm. The beam is folded by two reflecting mirrors 14 and 16 that provide adjustment of the laser beam position. The adjustment enables the beam axis to coincide with the physical optical axis of the illumination optics. The beam is then shaped by the pair of cylinder lenses 18 and 20 into a 192×77 µm elliptically shaped beam (at the $1/e^2$). The 192 µm dimension is formed by the 150 mm focal length cylinder lens 18, and it illuminates the long axis of the A-1 aperture 22 (which is parallel to the plane of the page in FIG. 1A). The 77 µm dimension is formed by the 60 mm focal length cylinder lens 20, and it illuminates the short axis of the A-1 aperture. The A-1 aperture is 653×89 µm. The illumination doublet 23 produces an elliptically shaped Gaussian intensity distribution of 37.4×12.6 µm in the flowcell 24. The minor axis of the ellipse is parallel to the direction of flow, which is vertical, i.e. in the direction of arrow 26.

Cells that pass through the measuring volume scatter and absorb the incident radiation. The light scattered and absorbed is captured and measured in the detection optics illustrated schematically in FIG. 1B. The unscattered light and the light that is scattered up to 19.5° is collected by the high numerical aperture (Hi—NA) lens 28 and collimated. The beam is divided into two parts by the 30/70 (30% reflection, 70% transmission) beamsplitter 30. The beam 32 is reflected onto a photodiode, and is used for the absorption measurement, while the transmitted beam 34 is further split by the 20/80 (20% reflection, 80% transmission) beamsplitter 36 to make the two scatter channels. The reflected scatter channel 38 has a 5°–15° darkstop 40, while the transmitted channel 42 has a 2°–3° darkstop 44. The light passing through each of these darkstops 40, 44 is then focused down through lenses 46 and 48 onto photodiodes 50 and 52, respectively. Neutral density filters 54, 56 and 57 are then used to reduce the light levels at each photodiode to a level that is appropriate for the standard detectors and preamplifiers.

The beam 32 is focused through lens 58 onto a detector/preamplifier 60. The preamplifier output is proportional to the optical power transmitted through the system. It collects unscattered light and light that is scattered into angles of up to about 19.5°. Within this angular interval, about 98% of the light scattered by sphered erythrocytes and reticulocytes is collected.

The absorption channel of the commercially available TECHNICON H·1 instrument is not optimized for measuring cellular absorption. The absorption signals are of the same level as the noise on the absorption preamplifier. A mathematical model of the absorption detection process was developed. This model predicted that the signal would improve dramatically with a decrease in the area of illumination by the laser in the flowcell. The size of the slit was reduced from a nominal 150×20 microns (on the TECHNICON H·1 system) to a nominal 40×20 microns to increase the signal to noise ratio by a factor of 3.75.

The signal (pulse height) from the absorption preamplifier is between 20 and 50 millivolts. This is much smaller than the signal processing electronics requires. A second gain stage was added to the absorption preamplifier with a gain of about 25. This brought the pulse heights up to about 1 volt.

The gain of the preamplifier circuit and optical density of the neutral density filter in each scatter channel were chosen to produce mean pulse signal levels of about 2 volts at the output of each channel when Technicon (TCN) Optical Test Material (OTM, TCH T03-1704) was assayed. OTM consists of sphered and hard fixed red blood cells. This material is commercially available from the assignee hereof, and is adapted for use on the TECHNICON H·1 system. This then allows fine adjustment of the overall gain in each channel using a variable gain amplifier in the post detection signal processing hardware.

Figure 1C:
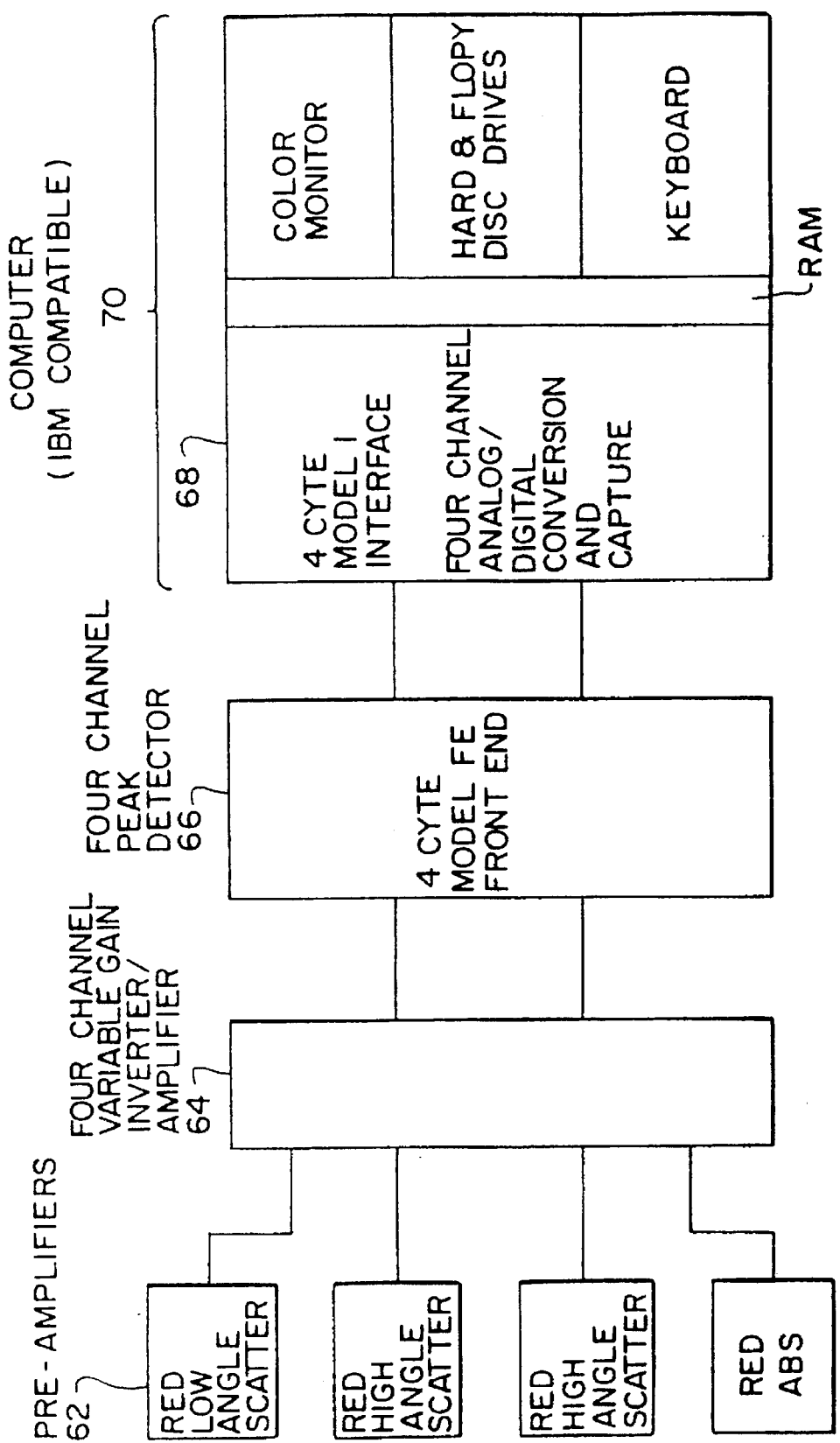

A functional block diagram of the post detection signal processing system is shown in FIG. 1C. The system consists of pre-amplifier 62, a variable gain amplifier 64, pulse height analyzer 66, analog-to-digital converter 68, and data acquisition hardware (computer) 70 and software.

The electronic systems for the system consist largely of the 4Cyte system available from Howard Shapiro, M.D., P.C., Cambridge, Mass., (4Cyte Model FE Front End and 4Cyte Model I Interface Card). The pulse-height analyzer, analog-to-digital converter and data acquisition software are all components of the 4Cyte system. These components produce held pulses representing the pulse heights for up to four input signals, and allow setting of the "valid" pulse height threshold level. The 4Cyte interface card is used in conjunction with the 4Cyte software for analog-to-digital conversion of up to four input signals, and the capture of those values in the RAM memory of the host computer. The digitized signals are stored in list mode. There are five eight-bit bytes of information for each cell, one for each of the four parameters measured, and one for flagging. The host computer for these experiments was an IBM PC/XT clone equipped with a color monitor and a math coprocessor. Data reduction can be performed on any IBM compatible computer.

The following examples set forth reagent compositions and methods incorporating the same for the identification of reticulocytes and characterization of reticulocytes and red blood cells using absorption flow cytometry techniques. Standard commercially available reagent grade materials were used whenever possible. It will be understood that the formulations and the procedures which follow are provided for purpose of illustration only, and that other ingredients, proportions and procedures can be employed in accordance with the disclosures of this invention.

EXAMPLE 1

Scatter and Absorption Measurements for Distinguishing Reticulocytes and Erythrocytes Within a Blood Sample Using a Reagent Composition and Method of the Present Invention Oxazine 750 dye was stored in a 1 mg/ml N, N-dimethylformamide stock solution. A working reagent was created by adding the dye stock to a buffer solution containing the following components at the concentrations noted:

| | |
|---|---|
| Oxazine 750 | 6 ug/ml |
| Calcium Chloride | 0.3 mM |
| Potassium Chloride | 4.0 mM |
| Magnesium Chloride | 88.0 mM |
| Sodium Phosphate (Tribasic) | 0.5 mM |
| Sodium Bicarbonate | 20.0 mM |

The final osmolality and pH of the working reagent used in this study were 272 mmol/kg and 8.1, respectively.

Samples were hand-mixed in a manner which simulated the automated TECHNICON H·1 system red cell sample processing scheme. Glass test tubes were filled with 5 milliliters of the working reagent. Five microliters of a blood sample were then pipetted into the reagent while the reagent was undergoing agitation on a vortex mixer. The 1:1000 dilution of blood was then fed into the sample line of the flow cytometric apparatus. In approximately two minutes the sample passed through the flow cell, and was then exposed to a helium-neon laser source for red cell and reticulocyte analysis. Each sample was measured in duplicate if the sample volume permitted. Microscopic examination revealed that most red cells and reticulocytes in this mixture were partially sphered.

At the completion of the analysis, the raw data was displayed in the form of a Red Scatter v. Red Absorption cytogram, FIGS. 2A–2D. Distinct cell populations were clearly observed based on their particular scatter and absorption signals. The erythrocyte population falls within Region A between the vertical axis and vertical line X. These cells show high scatter signals and low cell absorption signals. The major portion of the reticulocyte population falls within the region to the right of X, Region B. These cells are distinguishable from the mature erythrocytes due to the higher absorption signals from their Oxazine 750 stained RNA. The platelet population lies within Region C below line Y, and the coincidence region lies within Region D above line Z. The platelets have relatively low scatter signals when compared to the reticulocytes.

Figure 2B:
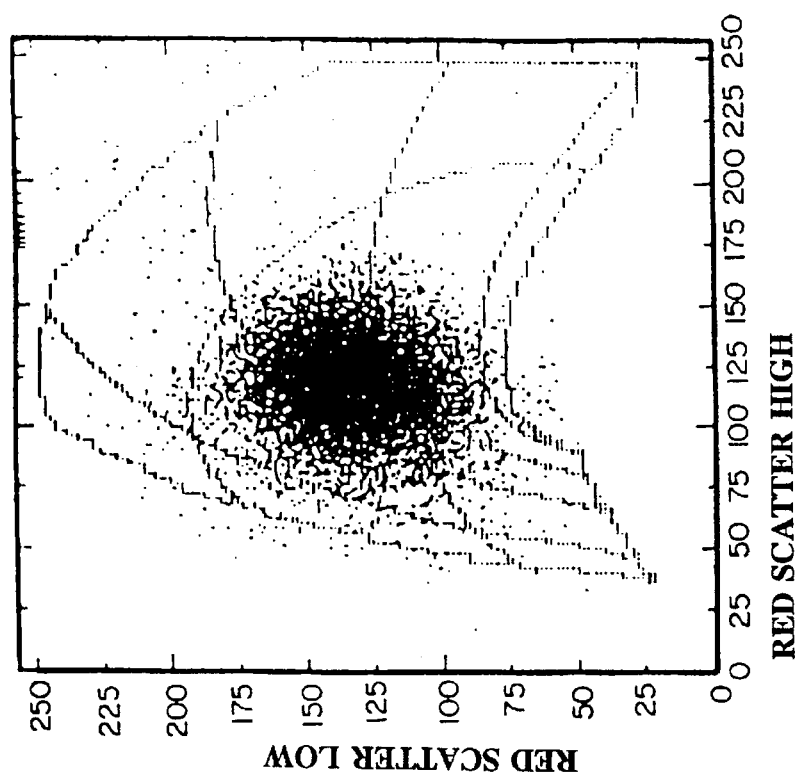
FIGS. 2B and 2D are cytograms of red light low angle scatter vs. red light high angle scatter for a whole blood sample containing partially sphered red cells and reticulocytes stained with Oxazine 750 and New Methylene Blue, respectively, in accordance with Example 1.
Figure 2A:
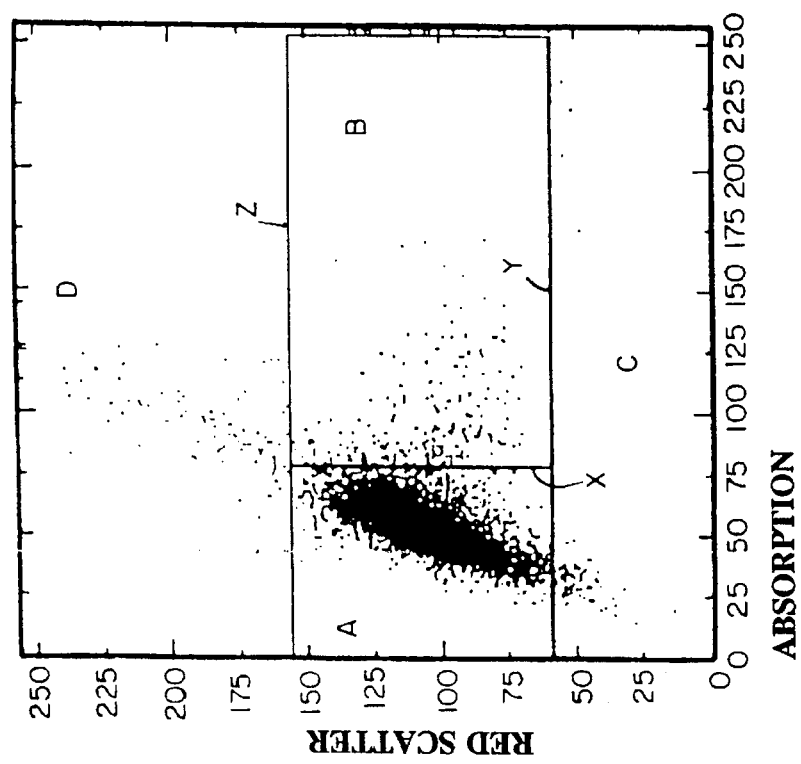
FIGS. 2A and 2C are cytograms of red light scatter vs. red absorption.
Figure 2D:
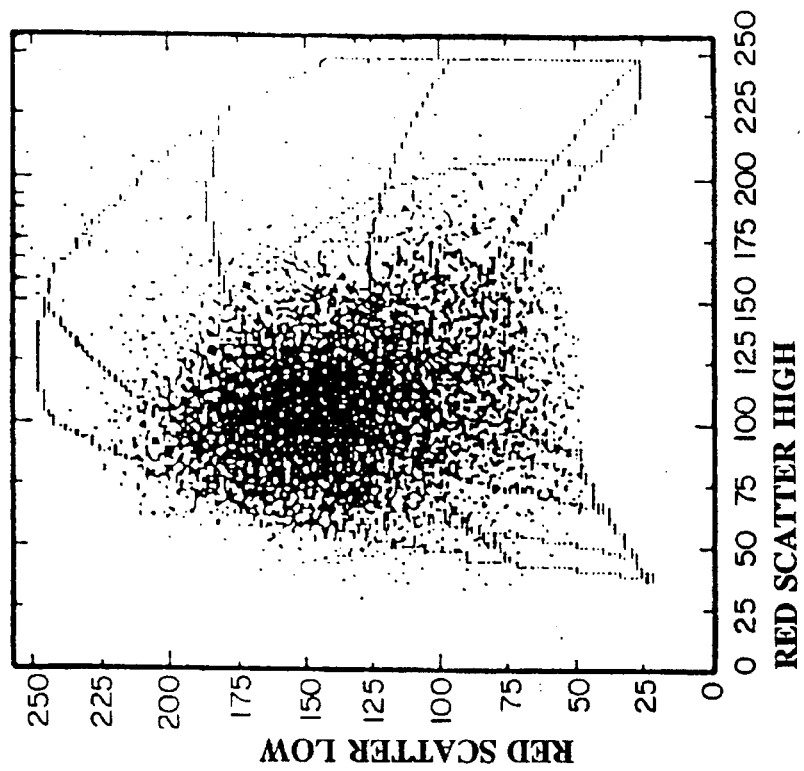

Based on the absorption separation between mature erythrocytes and reticulocytes, the reticulocyte count of a patient sample may be determined by creating electronic "windows" which define the ranges of scattered light and absorption which identify reticulocytes and erythrocytes. The number of reticulocytes and mature erythrocytes falling within each "window" are determined so that the percentage of the reticulocytes and erythrocytes present in the total cell population is then calculated. In FIG. 2A, the reticulocyte "window" is determined by Region B, and the mature erythrocyte "window" by Region A. Note, in FIG. 2B and in all following scatter/scatter cytograms, the non-linear grid overlaps indicate the loci of constant volume and constant refractive index for perfect spheres according to the above-noted method of Tycko.

The reference percentage of reticulocytes in each sample was determined using the manual microscopic procedure recommended by the National Committee for Clinical Laboratory Standards (NCCLS). In this procedure, a small volume of the sample was prepared, and the percentage of reticulocytes in the sample was counted with the aid of a microscope. The microscope was equipped with a 100X oil immersion objective and a 10X ocular. A minimum of 1000 cells were counted for each sample. A Miller disc was inserted in the ocular of the microscope to improve counting precision. Any red cell containing two or more particles of blue material after staining was labeled a reticulocyte.

The reticulocyte count of a patient sample was measured as 2.3% by this flow cytometric technique. The same blood sample was also analyzed by the NCCLS method. The result was a reticulocyte count of 1.7%.

Figure 2C:
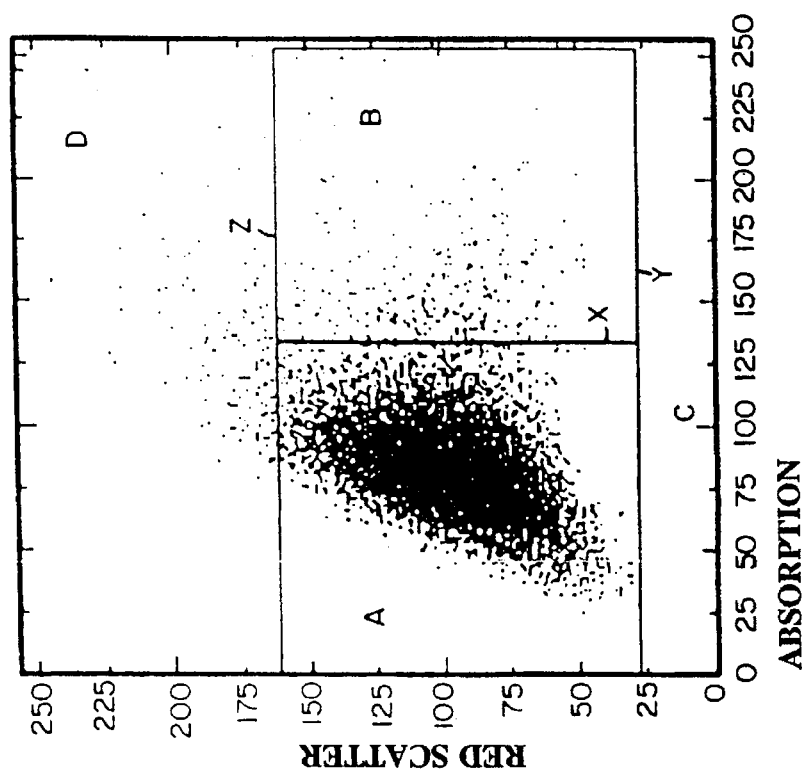

A second experiment was conducted to discriminate between reticulocyte and erythrocyte populations when cells were stained with New Methylene Blue and measured by the scatter/absorption flow cytometer. The buffer formulation was the same as that for the reagent composition containing Oxazine 750. The concentration of New Methylene Blue dye in the working reagent, which replaced the Oxazine 750, was 60 µg/ml. The sample preparation and analysis protocols as described above were followed. However, microscopic examination revealed that the red cells and reticulocytes were less sphered than in the Oxazine 750 mixture. The raw data from the analysis was displayed in the form of a Red Scatter v. Red Absorption cytogram (FIG. 2C). Note, in comparison to FIG. 2A, both the absorption and scatter signals are more spread out, presumably due to orientational noise. Based on the absorption separation between erythrocytes and reticulocytes, the reticulocyte count of the patient sample was measured as 2.2%. When analyzed by the NCCLS method, a reticulocyte count of 1.7% was obtained.

EXAMPLE 2

Scatter and Absorption Measurements for Distinguishing Reticulocytes and Erythrocytes Within a Blood Sample Using the Reagent Composition of Example 1 Containing a Zwitterionic Surfactant A second set of experiments was conducted utilizing the reagent compositions of Example 1, but further including a zwitterionic surfactant to isovolumentrically sphere the red blood cells and reticulocytes.

For each experiment, a working reagent was created by adding to the reagent composition the surfactant, lauramidopropyl betaine so that the final concentration of the surfactant in the reagent was 63 µg/ml.

The sample preparation as described above with regard to Example 1 was followed.

When viewed through a microscope, the mature red cells and reticulocytes in a prepared sample were found to be perfectly sphered and the reticulocytes stained. Note the difference between FIGS. 8A and 8B and FIGS. 2A–2D and 3A–3D which demonstrates increasing reduction in orientational noise with increasing completeness of sphering.

Figure 3B:
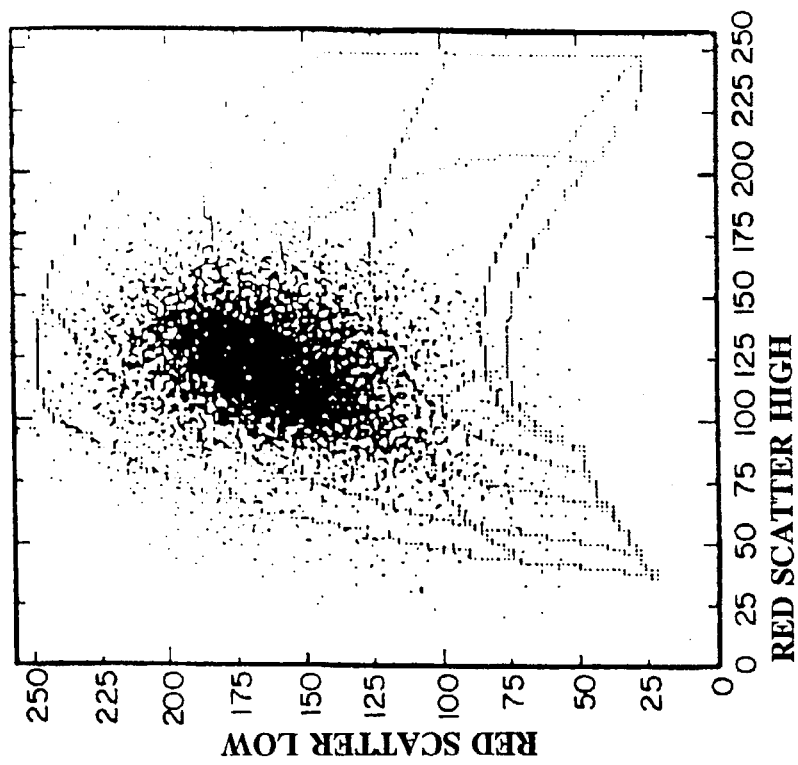
FIGS. 3B and 3D are cytograms of red light low angle scatter vs. red light high angle scatter for a whole blood sample containing completely sphered red cells and reticulocytes stained with Oxazine 750, and New Methylene Blue, respectively, in accordance with Example 2.
Figure 3A:
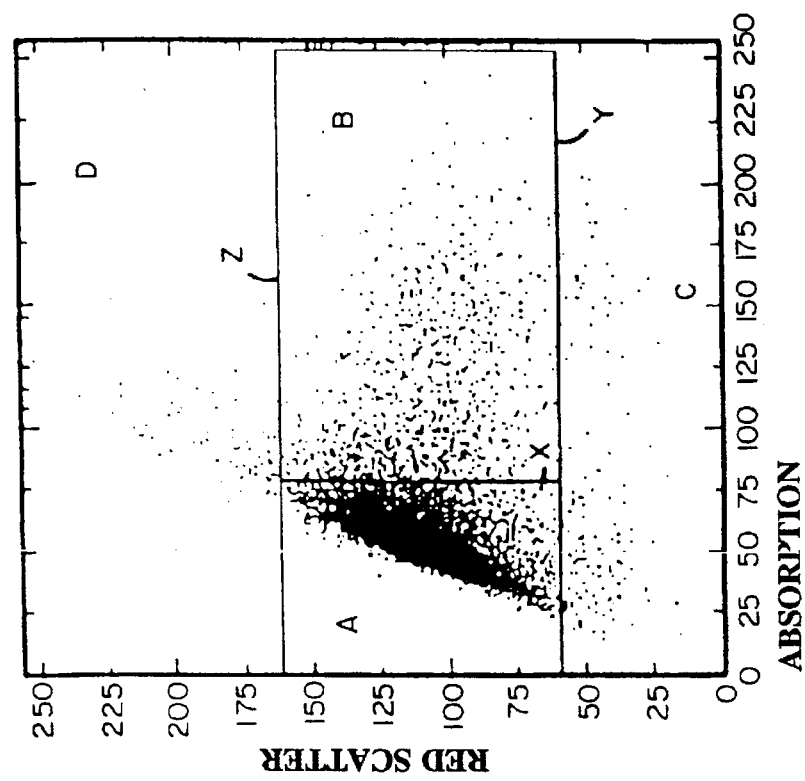
FIGS. 3A and 3C are cytograms of red light scatter vs. red absorption.
Figure 3D:
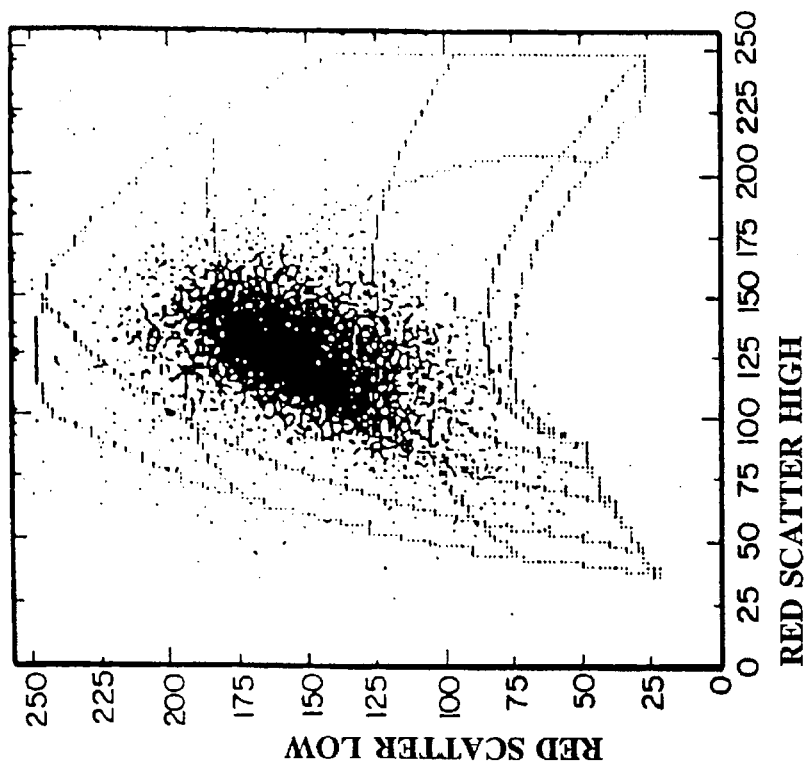

FIG. 3A demonstrates the higher degree of discrimination between reticulocyte and erythrocyte populations when cells were stained with the reagent composition containing the Oxazine 750 dye and above-noted surfactant. Note that in FIG. 8C, an unstained control, Region B is devoid of cells.

The reticulocyte count of a patient sample was measured as 8.0% by this technique. The same blood sample was also analyzed by the NCCLS method. The result was a reticulocyte count of 9.1%.

Figure 3C:
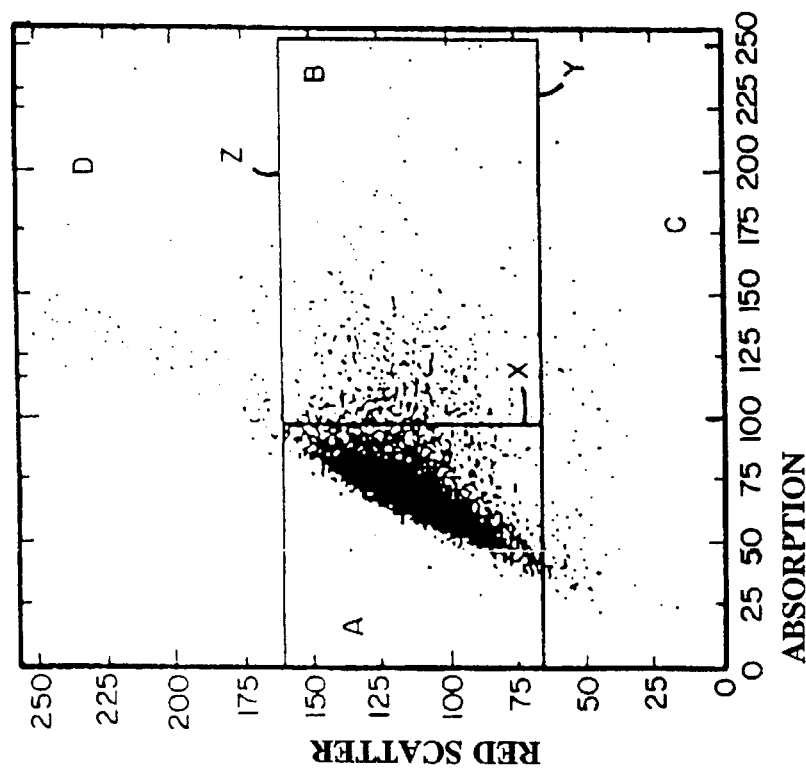

FIG. 3C demonstrates the degree of discrimination between reticulocyte and erythrocyte populations when cells were stained with the reagent composition containing the New Methylene Blue dye and above-noted surfactant.

The reticulocyte count of a patient sample was measured as 5.0% by this technique. The same blood sample was also analyzed by the NCCLS method. The result was a reticulocyte count of 9.1%.

EXAMPLE 3

Correlation Study with the Reagent Composition and Method of the Present Invention and the NCCLS Reference Method Using Absorption Data Corrected for Pseudo Absorption The detection optical subsystem collects both the scattered and unscattered light from cells passing through the laser beam in the flowcell. Cells scatter light into all directions. The relatively Hi-NA lens in the optical system, which is described above, accepts the light that is scattered into a cone that is centered on the optical axis with a half angle of up to 19.5 degrees. Thus, the light that is scattered into angles greater than 19.5 degrees is lost. As a result, when attempting to measure cellular absorption, completely non-absorbing cells "appear" to absorb up to a few percent of the incident light (pseudo-absorption). The measured absorption can be represented as follows:

$$\text{Absorption Signal} = \text{Pseudo-Absorption} + \text{Hemoglobin Absorption} + \text{Dye Absorption}$$

The pseudo-absorption signal of a mature red blood cell is typically of the same magnitude as the actual absorption signal from a stained reticulocyte. This reduces the degree of separation of the stained reticulocytes from the unstained red blood cells on the absorption cytogram. The signal to noise ratio of the absorption channel can be improved by correcting the signal to remove the pseudo-absorption and hemoglobin absorption components from each red cell and reticulocyte absorption signal. The amount of pseudo-absorption and hemoglobin absorption can be calculated for any given cell by using the well-known Mie light scattering theory described in the aforenoted Tycko patent. The scattering cross-section for the angular interval 19.5° to 180° plus the hemoglobin absorption component, $S_3$, can be calculated as follows:

$$S_3 = \pi a^2 Q_{ext} \cdot S(\lambda, n_s, \Theta_3, \Delta\Theta_3; V, HC)$$

where a is the radius of the sphered cell, $\lambda$ is the excitation (or illuminating) wavelength, $n_s$ is the refractive index of the sample stream and sheath, $Q_{ext}$ is the extinction efficiency of the cell, and for the case of pseudo-absorption, $\Theta_3 = 0°$, and $\Delta\Theta_3 = 19.5°$. $S_3$ values have been tabulated for all expected values of V and HC.

The pseudo-absorption correction is made as follows: The V and HC must first be determined from the two scattering signals from a cell from the scatter-scatter cytogram as described in Tycko. $S_3$ is then found in the look-up table entry for the measured V and HC, and subtracted from the value measured by the absorption channel. The result is the actual absorption due to staining of the cell. The measured absorption signal can be adjusted using the following relation to leave only the dye absorption for each cell:

$$\text{Dye Absorption} = \text{Absorption Signal} - \text{Hemoglobin Absorption} - \text{Pseudo-Absorption}$$
$$= \text{Absorption Signal} - S_3$$

For all data, the adjusted value is substituted for the raw data parameter prior to thresholding and flagging. Any objects whose red scatter parameters do not appear on the V-HC map are ignored in the data analysis scheme. This data is then redisplayed with the red scatter v. absorption cytogram reflecting the corrected values as shown in FIGS. 5A–5D.

A study was conducted to compare the performance of Oxazine 750 when used in a reagent composition in the scatter/absorption flow cytometer with the NCCLS manual method. Blood samples were stained with the reagent composition. Reticulocytes in the same set of blood samples were also counted using the NCCLS method.

The sample preparation and analysis protocols were the same as those described with regard to Example 2, except for the additional pseudo-absorption correction.

When viewed through a microscope, the mature red cells and reticulocytes in a prepared sample were found to be perfectly sphered and the reticulocytes stained.

Figure 6:
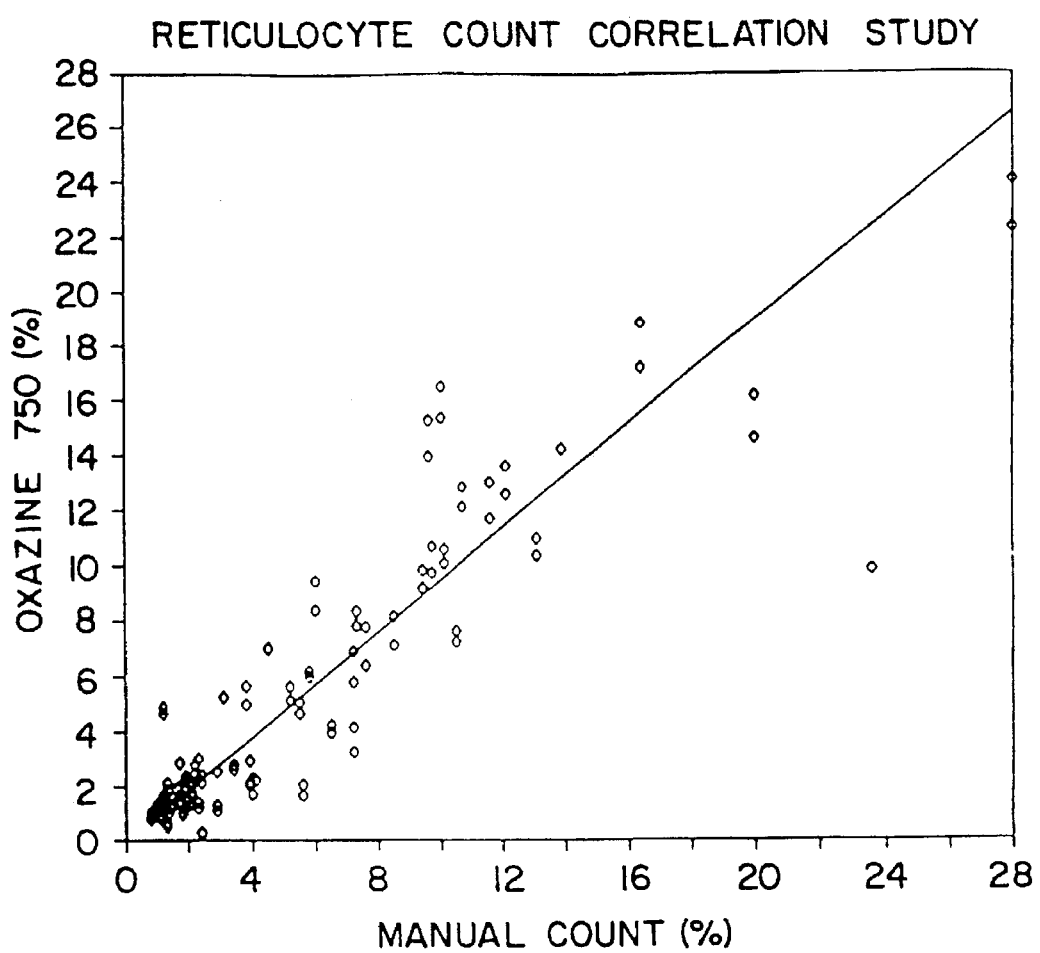
FIG. 6 is a comparison of the percentage of reticulocytes detected in a whole blood sample using the Oxazine 750 containing reagent of the present invention and the NCCLS reference method in accordance with Example 3.

The percentage reticulocyte counts obtained from these two methods are compared in FIG. 6. At a concentration of 2 µg Oxazine 750/ml in the reagent composition, close correlation was shown to exist between the measurements using the reagent composition and flow cytometric apparatus of FIG. 1A–1C, and those obtained by the NCCLS reference method. The correlation coefficient for the measurements as obtained by orthogonal regression analysis was 0.92.

EXAMPLE 4

Figure 4A:
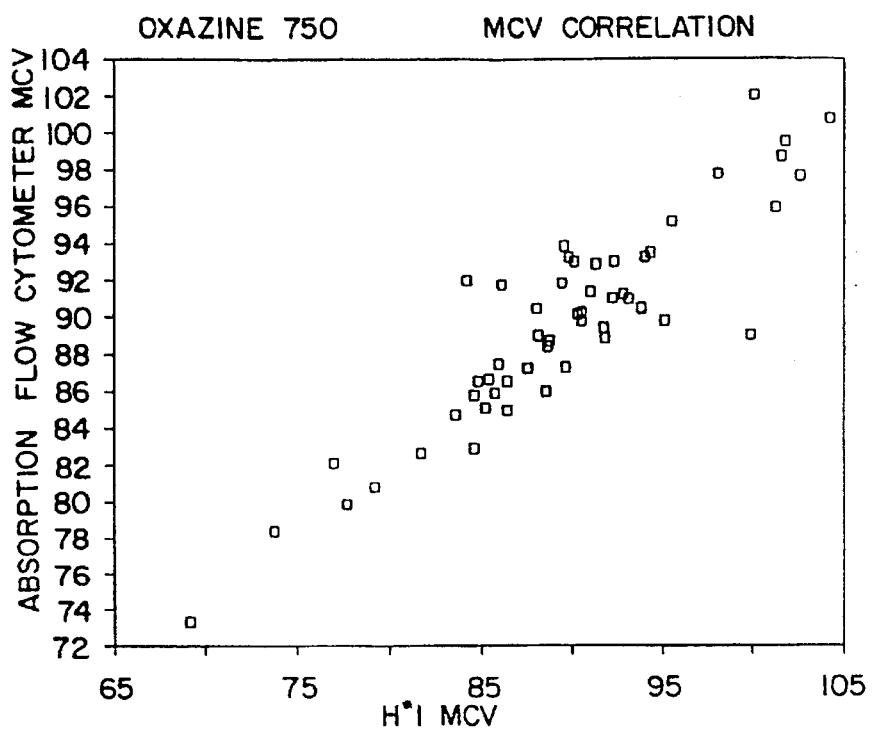
FIGS. 4A and 4B show the correlation between the MCV and MCHC data for reticulocytes stained with Oxazine 750 dye in accordance with Example 4.
Figure 4B:
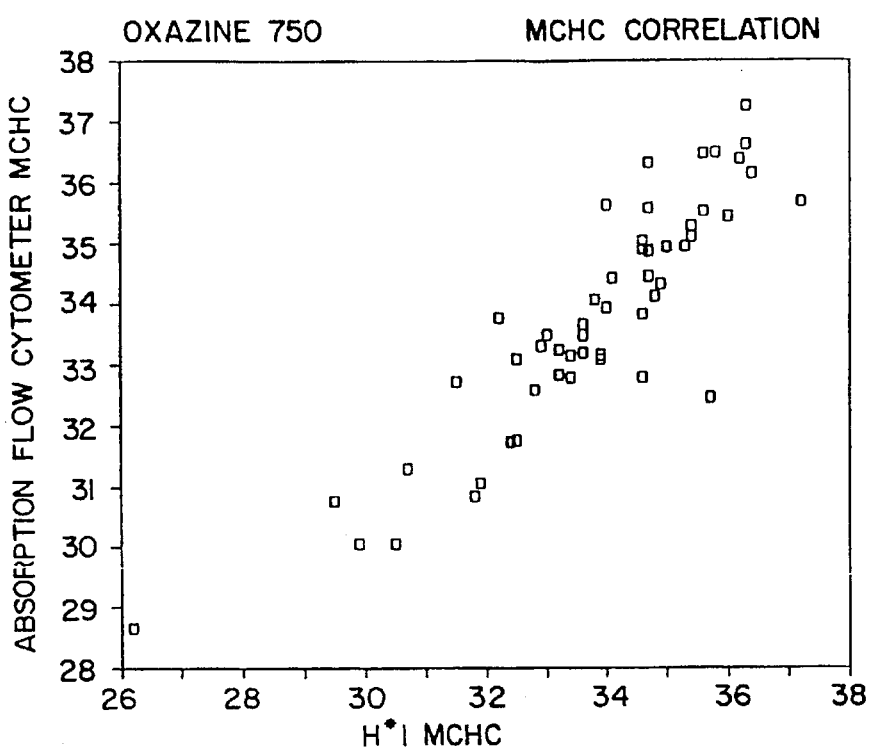
Figure 5D:
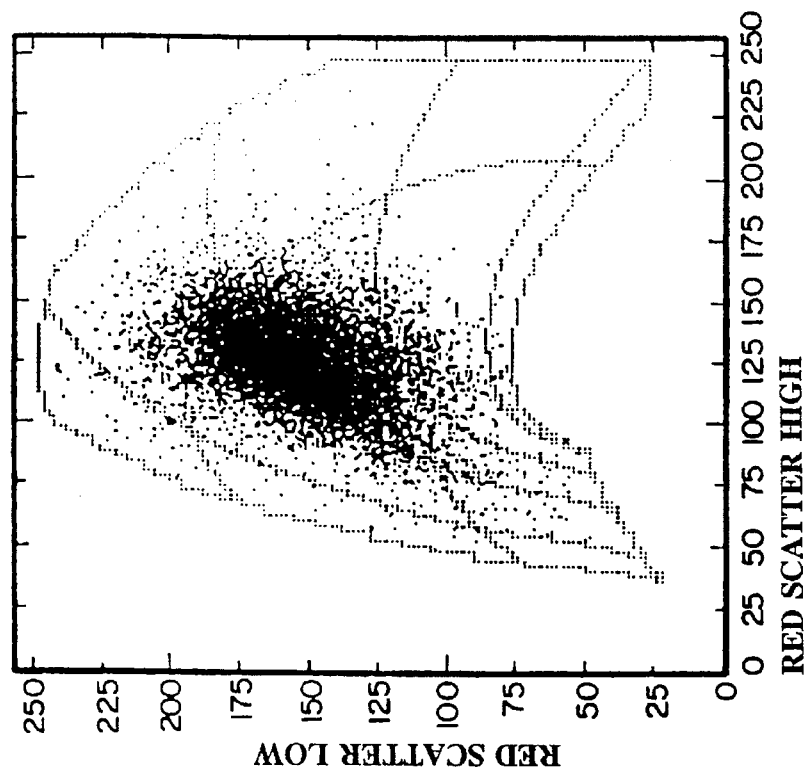
Figure 5C:
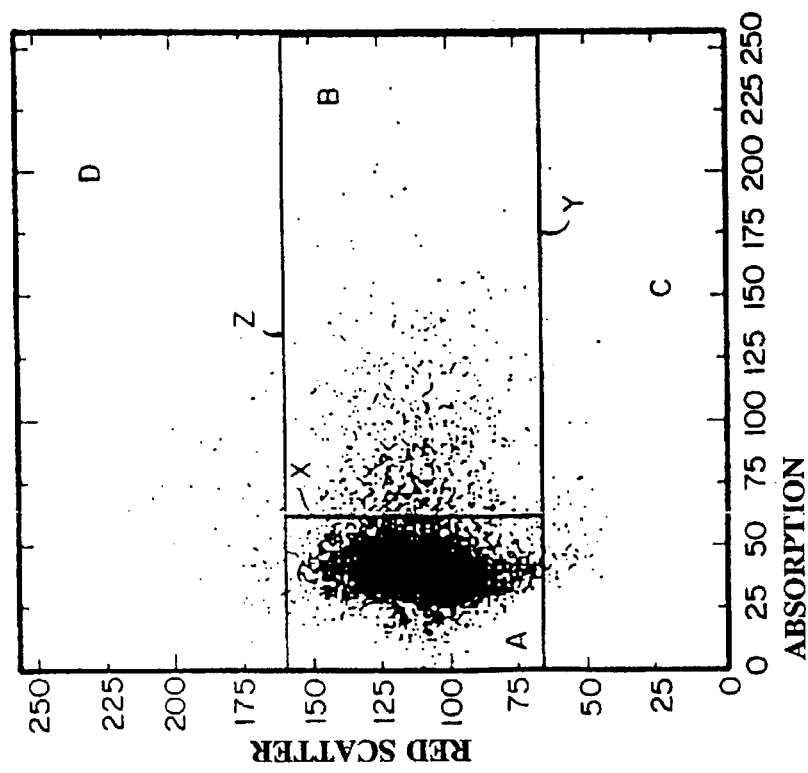

Correlation Study with the Absorption Flow Cytometer and the TECHNICON H·1 Reference Method Using Absorption Data Corrected for Pseudo-Absorption After pseudo-absorption correction and appropriate gating, the erythrocyte and reticulocyte indices, MCV and MCHC were separately determined and compared between the values obtained using the reagent composition of the present invention in the scatter/absorption flow cytometer and the TECHNICON H·1 measurements. FIGS. 4A and 4B show the correlation data for total red blood cell MCV and MCHC, respectively.

Figure 7:
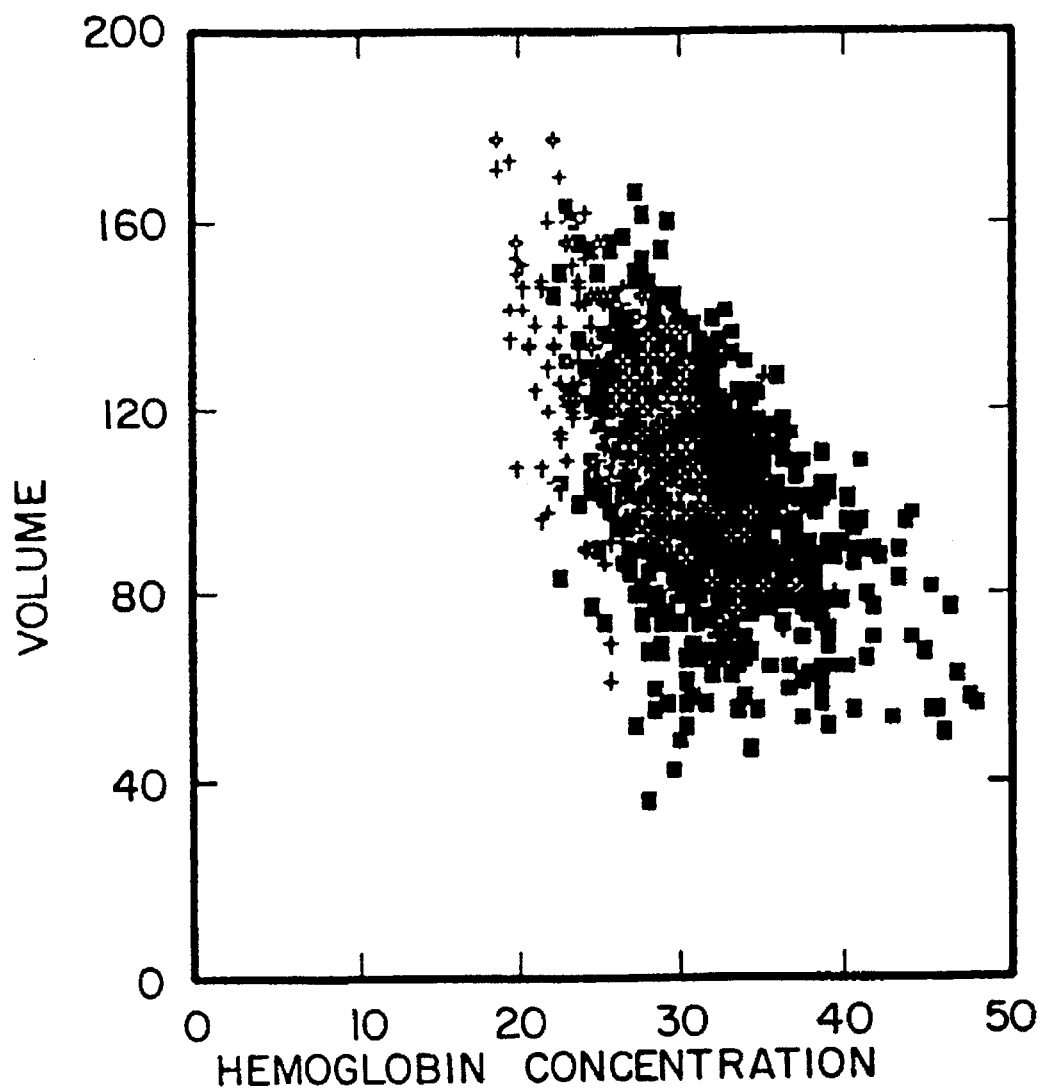
FIG. 7 is a cytogram of HC vs. V with reticulocytes identified by "+" and red cells as "−"

FIG. 7 shows reticulocytes marked as "+" in a HC vs. V cytogram.

Some advantages of the present invention evident from the foregoing description include a reagent composition and method for preparing a whole blood sample for electrooptical simultaneous quantitation of the volume, hemoglobin content and hemoglobin concentration of reticulocytes and erythrocytes by absorption flow cytometric techniques.

In view of the above, it will be seen that several objects of the invention are achieved, and other advantageous results obtained.

As various changes can be made in the above constructions and methods without departing from the scope of the invention, it is intended that all matter contained in the above description, or shown on the accompanying drawings, shall be interpreted as illustrative, not in a limiting sense.

What is claimed is:

1. A reagent composition for treating mammalian red blood cells in an anticoagulated whole blood sample which can be subsequently effectively measured electrooptically, said reagent composition comprising a zwitterionic surfactant as the sole surfactant which is a sphering agent that eliminates orientational noise when said sample is mixed with said reagent composition and is subsequently subjected to flow cytometric measurement, said surfactant present at a concentration effective to substantially sphere the mature erythrocytes and the reticulocytes in said whole blood sample without inducing cell lysis after mixing with said sample for at least 2 minutes; wherein said reagent composition does not include protein buffering or fixative; wherein the pH of the reagent composition is about 6 to about 9; and further wherein said reagent composition provides detection and discrimination of red blood cells and reticulocytes in said whole blood sample simultaneous with determination and measurement of hemoglobin content and concentration on a cell-by-cell basis.

2. The reagent of claim 1, wherein the concentration of zwitterionic surfactant is from about 3.0 µg/mL to about 148 µg/mL.

3. A reagent composition for the characterization of reticulocytes in an anticoagulated whole blood sample by flow cytometry; said composition comprising a dye compound in an amount effective for staining ribonucleic acid within the reticulocytes and a zwitterionic surfactant in an amount effective for isovolumetrically sphering the reticulocytes and erythrocytes without inducing cell lysis after mixing with said sample for at least 2 months; wherein said reagent composition does not include protein buffering or fixative; land further wherein the pH of the composition is about 6 to about 9.

4. The reagent composition of claim 3, wherein said dye compound is a cationic dye.

5. The reagent composition of claim 1 or claim 3, wherein said reagent composition comprises a solution having a tonicity of from about 0.5 to 2.0 times isotonic.

6. The reagent composition of claim 3, wherein the surfactant is present in an amount of from about 3.9 µg/mL to about 148 µg/mL.

7. The reagent composition of claim 1 or claim 3, wherein the sphering agent or surfactant is an alkyl betaine or an alkylamidobetaine.

8. The reagent composition of claim 6, wherein the sphering agent or surfactant is selected from the group consisting of lauramidopropylbetaine, cocoamidopropylbetaine, and cocoamidosulfobetaine.

9. The reagent composition of claim 1 or claim 3; wherein the sphering agent or surfactant is selected from the group consisting of N-tetradecyl-N, N-dimethyl-3-ammonio-1-propanesulfonate and N-dodecyl-N, N-dimethyl-3-ammonio-1-propanesulfonate.

10. The reagent composition of claim 1 or claim 4, wherein said pH is about 7 to about 8.

* * * * *